United States Patent [19]

Lorenz et al.

[11] Patent Number: 5,104,553

[45] Date of Patent: Apr. 14, 1992

[54] APPARATUS FOR FILTERING A REAGENT

[75] Inventors: Adrian Lorenz, Zurich; Heinz Scherrer, Rapperswil, both of Switzerland

[73] Assignee: Oerlikon-Contraves AG, Zurich, Switzerland

[21] Appl. No.: 286,563

[22] Filed: Dec. 19, 1988

[30] Foreign Application Priority Data

Dec. 23, 1987 [CH] Switzerland .................. 05016/87

[51] Int. Cl.$^5$ ............... B01D 35/00; B01D 37/04; G01N 33/00
[52] U.S. Cl. ................... 210/741; 210/104; 210/137; 210/141; 210/143; 210/251; 210/257.1; 210/258; 210/340; 210/341; 210/416.1; 210/744; 422/68.1; 422/73; 422/101; 436/10; 436/177
[58] Field of Search ............ 210/741, 744, 767, 806, 210/90, 104, 86, 134, 137, 141, 143, 257.1, 258, 340, 416.1, 251, 341; 422/68.1, 73, 101; 436/10, 177

[56] References Cited

U.S. PATENT DOCUMENTS

| | | |
|---|---|---|
| 3,143,393 | 8/1964 | De Seguin Des Hons . |
| 3,957,637 | 5/1976 | Morey .................................. 210/808 |
| 4,086,165 | 4/1978 | Formenti ............................. 210/104 |

FOREIGN PATENT DOCUMENTS 0107333 5/1984 European Pat. Off. .
1044781 6/1953 France .

Primary Examiner—W. Gary Jones
Attorney, Agent, or Firm—Sandler, Greenblum & Bernstein

[57] ABSTRACT

The filtering apparatus is used in combination with at least one analytical instrument, especially a particle analyzer and substantially comprises a controlled pump unit having an inlet side and an outlet side. The inlet side of the controlled pump unit is connected to a reservoir for a liquid medium to be filtered. The outlet side is connected to a filtering unit. An intermediate storage unit for intermediately storing the filtered liquid medium is connected to the filtering unit. The filtered liquid medium is fed to the analytical instrument from the intermediate storage unit which contains level detectors for detecting the liquid level in the intermediate storage unit. The level detectors are connected to a control unit for controlling the controlled pump unit.

37 Claims, 3 Drawing Sheets

APPARATUS FOR FILTERING A REAGENT

BACKGROUND OF THE INVENTION

The present invention relates to a new and improved construction of a filtering apparatus for use with at least one analytical instrument. The present invention also relates to a new and improved method of feeding a filtered liquid medium to at least one analytical instrument.

In its more particular aspects, the present invention specifically relates to a new and improved filtering apparatus for fine-filtering a liquid medium such as, for instance, a liquid reagent, a reagent solution, a solvent, a diluent or the like for use with at least one analytical instrument like, for example, at least one particle analyzer and is especially intended for use in the field of automated analyzers.

Particularly in the field of particle analysis it is highly significant whether the employed reagents as such are free of particles or contain only a very small number of particles. The reason therefore is that foreign particles falsify the analysis results in a manner similar to the known manner in which, for example, colored contaminants of solvents falsify the analytical results in colorimetry. When adhering to the example of colorimetric measurements, the colored contamination can be "eliminated" by a correcting reference or compensation measurement without any notable effort, however, when carrying out particle analysis, the problem is different and substantially more complex.

Generally, such particle analysis comprises a true counting process during which the particles are individually detected. Contrary thereto, there is only drawn an indirect conclusion with respect to the concentration or the amount of a compound which is contained in a solution or the like, when utilizing an optical measurement, i.e. a measurement relying upon measuring a statistical average. Furthermore, during particle analysis, there is in general simultaneously also measured the size of the particles in addition to the number of particles so that a measuring operation which measures "en bloc" or bulk properties like, for example, the optical absorption or extinction, cannot be utilized. Thus the particle analysis constitutes a type of measurement which can be associated with spectroscopy and its problems rather than measuring methods which determine the measuring result in a single measuring operation in terms of time. In correspondence therewith, the problems caused by interfering factors which affect the measurement or the measuring result, are of higher complexity and thus much more difficult to eliminate. Therefore, the direct compensation using known methods such as the comparison with a reference could not succeed in the field of particle analysis.

Thus, it is still required to utilize high-purity liquid media such as reagents, reagent solutions, solvents and diluents or the like in order to obtain acceptable "blank counts" for particle analysis. The term "blank count" is the term designating the number and size distribution of a residual amount of foreign particles which can not be eliminated.

In this connection, however, other problems arise which are not directly connected with the actual measuring operation but rather with the operation preceding the actual measurement. The preparation of liquid media such as reagents, nearly or totally free of particles, does not as such constitute a problem and there can be no doubt that products which have been prepared and placed into their containers, in fact, satisfy the requirements of modern and particularly automated particle measuring techniques. However, this situation is basically changed when such liquid media like reagents, reagent solutions, solvents or diluents are handled in greater volumes as required, for example, in automatic analyzers having sufficiently large reservoirs. A further decisive aspect is the following:

The reagents or reagent solutions which are used during particle analysis, are nearly totally made up of the solvent, for example, water which in general comprises well over 90 percent of the total volume. Thus, manufacturers would tend to, for instance, offer and ship vehicle-free pre-mixed compositions, i.e. concentrates which contain only small amounts of solvent, unless there would not exist the problem of properly and ultimately still carrying out quite expensive processing of the concentrate in order to obtain the utilizable liquid medium such as the reagent, reagent solution or the like. These are true limits which restrict the selection of available possibilities.

Generally, a liquid phase is freed from solid materials, specifically particles contained therein by means of filtration. The filtering procedure, however, constitutes a rather slow process which is better suited for a batch operation as compared to a continuous operation. However, whenever a filtering operation is intended to be included in a continuous operation, quite a series of compromises have to be made and one of the main compromises is the significant overdimensioning of the filtering apparatus inclusive of the pump used for the filtering operation. One of the reasons therefore is that, in a continuous process, a filtering location constitutes a bottleneck. This is still true in those cases in which the process constitutes merely a quasi-continuous process comprising a number of discontinuous steps which are carried out at a high repetition rate.

In specific cases of particle analysis, for example, hematology, the capability of detecting progressively smaller particles by the particle analysis gains increasing importance. During cancer therapy or treatment, for instance, for controlling the course of pathological cell disorders, the specific capability or particle analysis in the region of very small or submicron particles would significantly extend existing possibilities. However, there would naturally result correspondingly increased requirements concerning the utilized liquid media such as reagents, reagent solutions, solvents, diluents and the like which then must be freed from such very small or submicron particles. Such particles previously have been considered immeasurably small and their presence would markedly disturb the particle measurement or analysis in this particle size range. Ultimately this may result in the fact that the presently usual ready-to-use liquid media which are supplied, for example, in cubitainers, can no longer be provided in the required quality. Thus the available ready-to-use liquid media merely would be at a pre-stage of the required purity and thus could no longer be used as such.

When intending to introduce into particle analysis the filtering of liquid media such as reagents, reagent solutions, solvents, diluents and the like containing particles in the submicron size range, there would have to be provided a filtering apparatus in conjunction with the particle analyzer, in the first place. Additionally and in the second place, such filtering apparatus would have to be a specific filtering apparatus which would have to be specifically constructed for this purpose and which would have to satisfy the following criteria:

a. At every instant of use, there would have to be present a sufficient amount of the liquid medium such as the reagent, reagent solution, solvent, diluent or the like;

b. This sufficient amount or volume of the liquid medium would have to be freshly filtered at each instant of use in order to eliminate or minimize as far as possible any interim contamination, i.e. this sufficient amount or volume would have to be subject to extremely short storage periods; and c. The limiting filtering frequency, i.e. the maximum possible filtering rate of the filtering apparatus should be above the limiting frequency of the automatic analyzer, i.e. above the maximum possible throughput of one or more automatic analyzers which are connected to the filtering apparatus. This requirement corresponds to the filtering capacity or power which must be offered by the filtering apparatus.

It will be immediately evident that the aforementioned individual requirements diametrically oppose or counter each other at least in part.

SUMMARY OF THE INVENTION

Therefore, with the foregoing in mind it is a primary object of the present invention to provide a new and improved construction of a filtering apparatus for use with at least one analytical instrument and which filtering apparatus directly supplies filtered liquid media such as reagents, reagent solutions, solvents, diluents and the like which are utilized in the analytical instrument.

Another and more specific object of the present invention is directed to the provision of a new and improved construction of a filtering apparatus for use with at least one analytical instrument and which filtering apparatus can be operated on line with the analytical instrument.

Still a further significant object of the present invention is directed to a new and improved filtering apparatus which can be directly used on line with at least one automatic particle analyzer.

Another still important object of the present invention is directed to a new and improved method of feeding a filtered liquid medium such as a reagent, reagent solution, solvent, diluent or the like to at least one analytical instrument such as a particle analyzer, and which method permits filtering the liquid medium directly on line with the operation of the analytical instrument.

Now in order to implement these and still further objects of the invention, which will become more readily apparent as the description proceeds, the filtering apparatus of the present development is manifested, among other things, by the features that, the filtering apparatus comprises a controlled pump unit which is connected on its input side to a reservoir for a liquid medium to be filtered and, on its output side, to a filtering unit. This filtering unit is connected with an intermediate storage unit or vessel for intermediate storage of the filtered liquid medium which is supplied to the at least one analytical instrument from the intermediate storage unit or vessel. Level detection means for detecting the liquid level are provided in the intermediate storage unit or vessel and are connected to a control unit for controlling the controlled pump unit.

As alluded to above, the invention is not only concerned with the aforementioned apparatus aspect, but also relates to a new and improved method of feeding a filtered liquid medium to at least one analytical instrument, for example, at least one particle analyzer.

To achieve the aforementioned measures, the inventive method, in its more specific aspects, comprises the steps of:

controlling a supply pump, i.e. a controlled pump unit for pumping the liquid medium to be filtered as a function of parameters related to the measured liquid level changes in the intermediate storage unit or vessel; and further controlling the supply pump by parameters related to the measured pressure variations at the filtering unit, i.e. the filter elements which are arranged between the intermediate storage unit or vessel and the supply pump.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Figure 3:
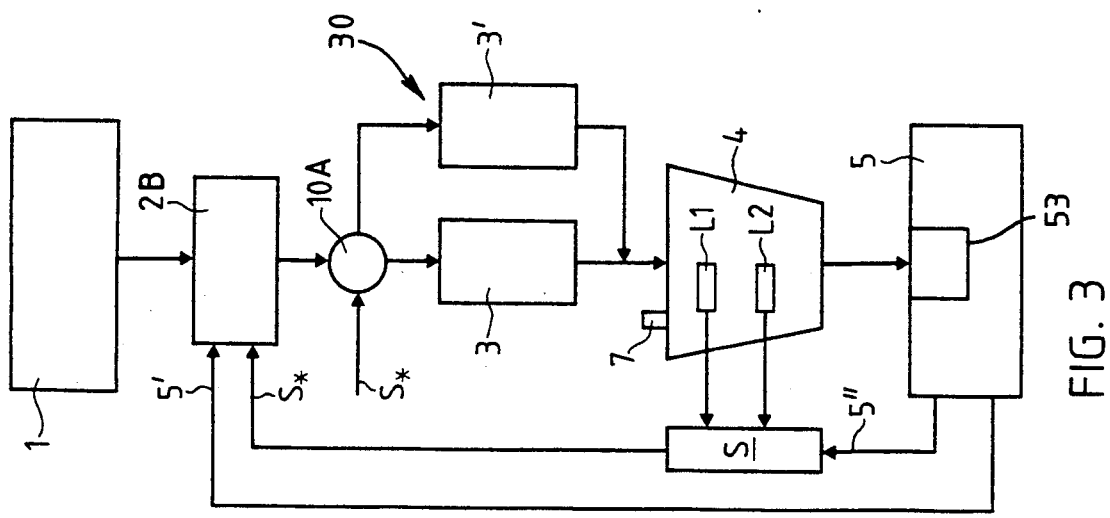
FIG. 3 is a schematic block diagram showing a third exemplary embodiment of the inventive filtering apparatus similar to the filtering apparatus shown in FIG. 2 but containing a different type of controlled pump unit and different liquid flow control means.

Describing now the drawings, it is to be understood that only enough of the construction of the filtering apparatus has been shown as needed for those skilled in the art to readily understand the underlying principles and concepts of the present development, while simplifying the showing of the drawings. Turning attention now specifically to FIG. 1 of the drawings, the filtering apparatus illustrated therein by way of example and not limitation will be understood to be used in conjunction with a particle analyzer 5. However, it will be further understood that the use of the inventive filtering apparatus in conjunction with the particle analyzer 5 represents an advantageous use of such filtering apparatus and such can also be very effectively used in combination with many other types of analytical instruments like, for example, spectrometers, liquid chromatographs and others in all cases which the operation of such analytical instrument requires the use of liquid media which are at least nearly free of suspended particles in the very small or submicron size range.

Furthermore, the inventive filtering apparatus can be constructed and dimensioned such as to supply the filtered liquid medium to more than one analytical instrument, for example, a plurality of particle analyzers which may include different types of particle analyzers, as well as a plurality of different types of analytical instruments.

Continuing, a reservoir or container 1 contains an unfiltered or prefiltered liquid medium such as a reagent, a reagent solution, a solvent, a diluent or the like in an amount sufficient for continuous operation during, for example, one day. It will be assumed that the unfiltered or prefiltered liquid medium contained in the reservoir or container 1, does not satisfy the purity requirements with respect to the absence of the aforementioned very small or submicron particles and must be further processed in order that the thus processed liquid medium can be utilized for analysis. Such processing operation is carried out "on-line" with the analytical instrument such as the particle analyzer 5 using the subsequently described inventive filtering apparatus.

This inventive filtering apparatus comprises as its main components, a controlled pump unit or filtering pump 2, a filtering unit 30, an intermediate storage unit or vessel 4, and a control unit S which effects control of operation through a control circuit incorporating the aforementioned main components of the inventive filtering apparatus. The controlled pump unit or filtering pump 2 removes the unfiltered or prefiltered liquid medium from the reservoir or container 1 and pumps the same under adequate pressure into the filtering unit 30 which comprises a filtering insert containing, for example, submicron-pores. Very frequently, during a filtering operation, the liquid medium which is placed upon such filtering insert, is sucked therethrough, i.e. the controlled pump unit or filtering pump 2 does not apply pressure to the filtering insert but draws the liquid medium therethrough by generating a pressure difference below the filtering insert. This very frequent conventional manner of filtration has advantages with respect to automatically limiting the operative pressure acting upon the filtering insert to approximately one atmosphere and excluding damage due to overpressure.

In the inventive filtering apparatus, the aforementioned advantages are not utilized and the power or pumping pressure of the controlled pump unit or filtering pump 2 is directly applied to the filtering surface of the filtering insert in the throughflow direction of the filtering unit 30. When utilizing this measure, there can be prevented that very small or submicron particles which may be formed in the controlled pump unit or filtering pump 2, for instance, due to abrasion, are directly flushed into the analytical instrument such as the particle analyzer 5. Furthermore, there are avoided the formation of foam and cavitation or bubble formation which can lead to problems in the intermediate storage unit or vessel 4 during the outfeed of aliquots of the filtered liquid medium from the intermediate storage unit or vessel 4 to the analytical instrument such as the particle analyzer 5. The operative relationship between the pump, the pump power and the type of filter, its surface and flow resistance as well as the absorption characteristic to be adjusted relative to the intermediate storage unit or vessel 4 will be discussed further hereinbelow.

The intermediate storage unit or vessel 4 has a comparatively small volume and the volume of filtered liquid medium contained therein is regulated by means of the control unit S and the level detection means which are provided in the intermediate storage unit or vessel 4. The intermediate storage unit or vessel 4 constitutes a short-time reservoir and is protected against contamination by constituting a substantially closed vessel which communicates with the atmosphere only through a deaeration filter 7. The level detection means comprise two detectors, namely a high level detector L1 and a low level detector L2. Furthermore, the intermediate storage unit or vessel 4 is constructed for easy maintenance; particularly, the intermediate storage unit or vessel 4 is constructed such that it can be rapidly rinsed or, if desired, exchanged and does not contain any locations like corners and slits which are prone to the accumulation or entry of contaminants. The intermediate storage unit or vessel 4 supplies the filtered liquid medium such as the reagent, reagent solution, solvent, diluent or the like to a receiving unit 53 which is associated with the analytical instrument such as the particle analyzer 5 but may also be located in such analytical instrument.

The foregoing discussion is believed to be sufficient for explaining the basic principle of the construction and operation, i.e. controlled flow of the liquid medium required for carrying out the desired analysis, of the inventive apparatus. Prior to discussing the specific embodiments shown in FIGS. 2, 3 and 4, there will be first discussed hereinbelow some much-used terms in the field of particle analysis with reference to FIGS. 5 through 7.

Figure 5:
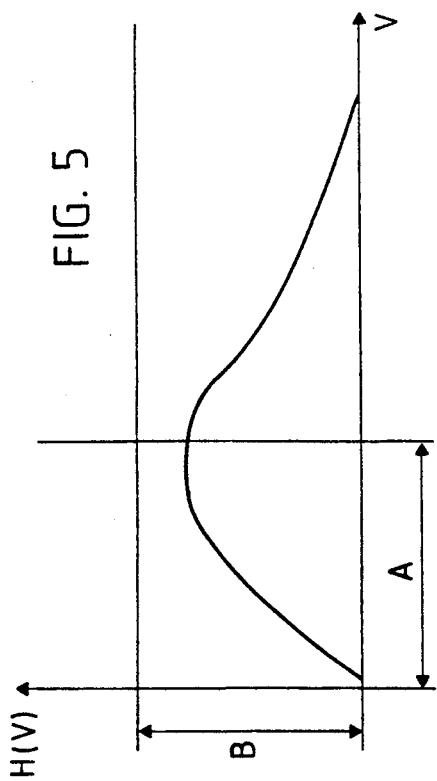
FIG. 5 is a diagram generally showing the number or frequency of occurrence of particles as a function of the particle volume and indicating the very small or submicron particle range.

FIG. 5 shows a diagram of the general type obtained as a result of a particle analysis and which diagram is frequently referred-to as a histogram. In such diagram, the number or the frequency o occurrence H(V) of particles is plotted as a function of the particle volume V. The particle volume range designated by the reference character A denotes the very small or submicron particle range which, when considering blood particle analysis, presently is of particular interest because it relates to blood platelets or thrombocytes. However, it is this particular very small or submicron range of particle size in which the aforediscussed foreign particles particularly strongly interfere with the particle analysis and may render questionable the unambiguity of the particle analysis or measurement.

The reference character B in FIG. 5 designates the number or count of particles or the frequency of occurrence of particles. When carrying out the aforementioned blood particle analysis, even the smallest amounts, i.e. number or counts or frequencies of occurrence of thrombocytes or platelets are significant, for instance, during cancer therapy or treatment. However, in this range B correspondingly small foreign particles become noticeable numerically, i.e. enter into the measured number or count or frequency of occurrence of particles. The number or count or frequency of occurrence of particles in the range B is significant, for example, for detecting the disappearance or destruction of cells, particularly thrombocytes or platelets, due to the cancer therapy or treatment if the required therapeutical measures like, for example, transfusions are intended to be initiated in time, or if it is intended to optimally control the dosage of a chemotherapeutical agent during chemotherapy in consideration of all the known side effects. When the related criteria, therefore, can be reliably determined by corresponding measurements, there will be available for diagnosis as well as therapy the means for selecting and selectively directing life-saving or at least life-prolonging measures.

Figure 6:
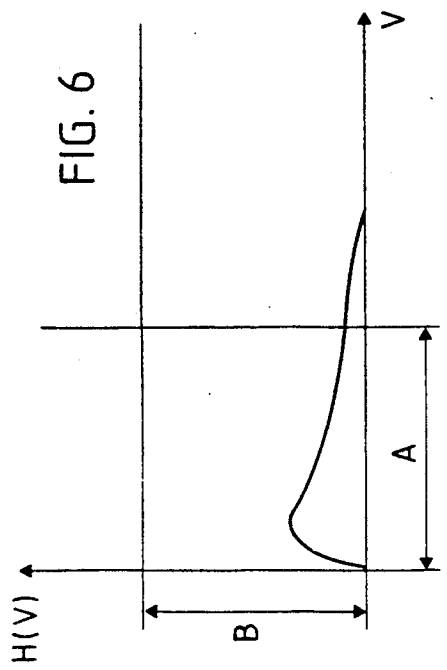
FIG. 6 is a diagram showing the number or frequency of occurrence of particles as a function of particle volume in an unacceptable blank count obtained when using a liquid medium containing foreign particles.

The diagram illustrated in FIG. 6, like the diagram of FIG. 5, shows the number or count or frequency of occurrence H(V) of particles as a function of the particle volume V. The specific range A of very small or submicron particles and the range B of the number or count or frequency of occurrence of particles of interest are also indicated in FIG. 6. The particular example illustrated in FIG. 6 is the example of an unacceptable blank count. Such unacceptable blank count is also illustrated in the print-out II of FIG. 7. The print-out I of FIG. 7 relates to an acceptable blank count of the type as obtained for a filtered liquid medium when using the inventive filtering apparatus.

Figure 7:
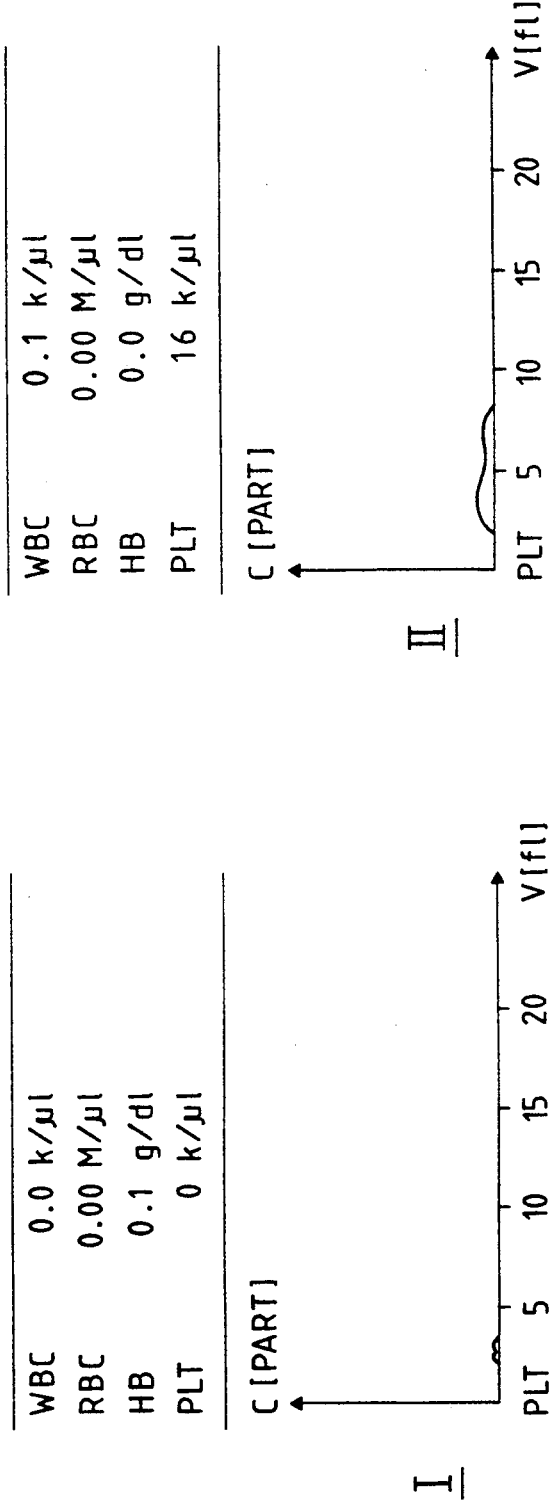
FIG. 7 shows two print-outs I and II obtained from a haematological instrument and wherein the print-outs I and II have been obtained respectively in the presence and in the absence of a filtering apparatus of the type as shown in FIGS. 1 through 4.

The print-outs I and II in FIG. 7 respectively show the histogram of the filtered liquid medium obtained when using the inventive filtering apparatus and the unacceptable blank which produced the diagram schematically illustrated in FIG. 6. The graphs of the print-outs I and II constitute plots of the number or counts of particles C[PART] as a function of particle size V[fl] measured in femtoliters for the example of blood particle analysis, specifically platelet PLT particle analysis. The print-outs I and II also give the numerical result of the particle analysis in $k/\mu l$, i.e. thousands per $\mu l$ with respect to white blood cells WBC and platelets PLT, in $M/\mu l$, i.e. millions per $\mu l$ with respect to red blood cells RBC, and in g/dl, i.e. gram per dl with respect to haemoglobin HB.

The unacceptable blank count as illustrated in FIG. 6 and the print-out II in FIG. 7, shows a high proportion of particles in the very small or submicron range A of particle sizes so that, when using such liquid medium, the sensitivity threshold for platelet or thrombocyte measurements is undesirably upwardly shifted due to the presence of this interfering background. Contrary thereto, as will be apparent from the print-out I in FIG. 7, the acceptable blank count shows a liquid medium which is nearly free of very small or submicron particles.

Consequently, therefore, when using such acceptable filtered liquid medium, the particles indicated by such diagram or histogram obtained as a result of an actual particle analysis, are analytically relevant and permit reliable interpretation. When using a liquid medium of the type producing the diagram or histogram illustrated in FIG. 6 and the print-out II in FIG. 7, there will be considerable uncertainty as to whether relevant particle data are buried under the data obtained for the foreign particles. At this point the importance of using liquid media such as reagents, reagent solutions, solvents, diluents or the like which are substantially free of foreign particles, will be apparent from the foregoing explanations. However, additionally there will also be apparent the problems which are encountered when such high standard is intended to be realized for the liquid medium.

When considering the functional course of operation of the entire installation, it will be assumed that a sufficiently large volume of filtered liquid medium having the shortest possible storage time can be withdrawn from the intermediate storage unit or vessel 4 at any time. The liquid medium is withdrawn from the intermediate storage unit or vessel 4 in aliquots or portions and in accordance with an overriding sequence of operating steps or cycles, such as, for instance, the operating steps or cycles of the analytical instrument such as the particle analyzer 5.

Based on this assumption, in the ideal case, the intermediate storage unit or vessel 4 should be empty after one withdrawal of liquid medium. However, even in the event of a deviation from the normal sequence of operating steps or cycles, the intermediate storage unit or vessel 4 should be sufficiently filled immediately after withdrawal in order to permit supplying the extra amount or volume of liquid medium required due to the deviation from the normal sequence of operating steps or cycles. Countering this requirement, however, is the operational behavior of the filtering unit 30 which, in effect, represents a bottleneck and also has dead-times during its operation. As a consequence, the intermediate storage unit or vessel 4 is designed with a volume exceeding the withdrawal volume by a factor greater than 1.0 and there is established a volume difference operation which functions as explained hereinbelow.

At the liquid level of the high level detector L1, the intermediate storage unit or vessel 4 contains an amount or volume of liquid medium which corresponds to, for example, 1.5 times the absorption or take-up volume of the receiving unit 53 in the analytical instrument such as the particle analyzer 5. At this state, the controlled pump unit 2 is deactivated. When the liquid level in the intermediate storage unit or vessel 4 falls below the high level sensor L1 due to the operation of controlled pump unit or filtering pump 2 is energized. As a consequence, freshly filtered liquid medium flows into the intermediate storage unit or vessel 4 during the withdrawal of the liquid medium therefrom into the receiving unit 53 of the analytical instrument such as the particle analyzer 5. This is true for all of the embodiments illustrated in FIGS. 1 through 4.

Generally, the withdrawal rate will be higher than the inflow rate from the filtering unit 30 so that the liquid level in the intermediate storage unit or vessel 4 continuously falls and approaches the level defined by the low level detector L2. When the liquid level has dropped to that of the low level detector L2, one or more by-pass filters or filter elements 3' and/or 3" are automatically switched on or activated in the embodiments shown in FIGS. 2 through 4 and thereby the filtering power or capacity is doubled or multiplied for a short period of time. In this manner there is realized a flexible supply of liquid medium under the condition that the volume of the intermediate storage unit or vessel 4 is approximately equal to the absorption or take-up volume of the receiving unit 53 in the analytical instrument such as the particle analyzer 5. This flexibility in the supply of freshly filtered liquid medium also results in the highly desired operational reliability at the occurrence of deviations from the normal sequence of operating cycles. At the same time, there are beneficially achieved minimum storage or dwell times which, in fact, last only for one operational cycle.

Figure 2:
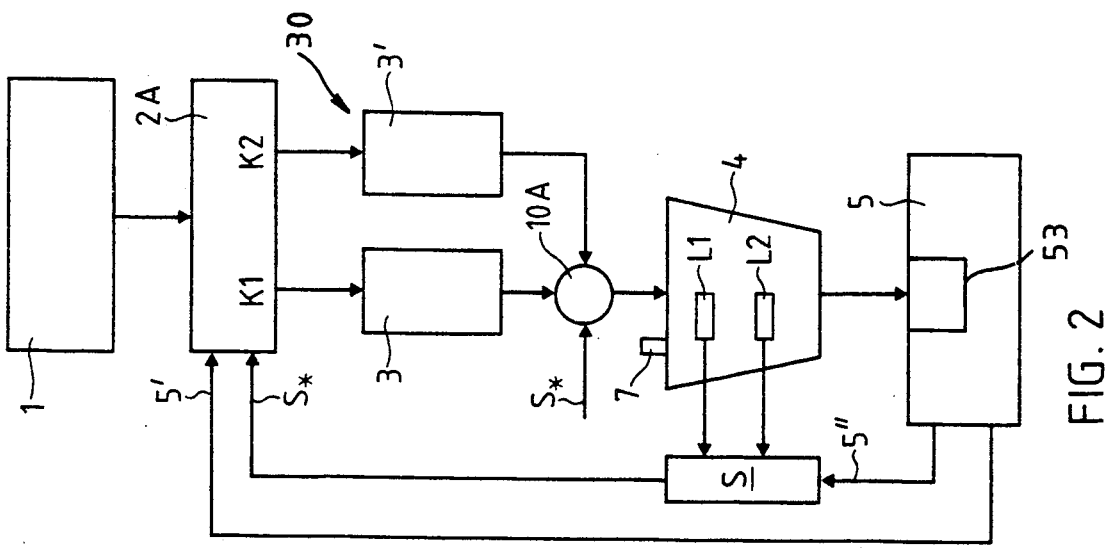
FIG. 2 is a schematic block diagram of a second exemplary embodiment of the inventive filtering apparatus containing a specific type of parallel connection between two filter elements of a filtering unit.
Figure 4:
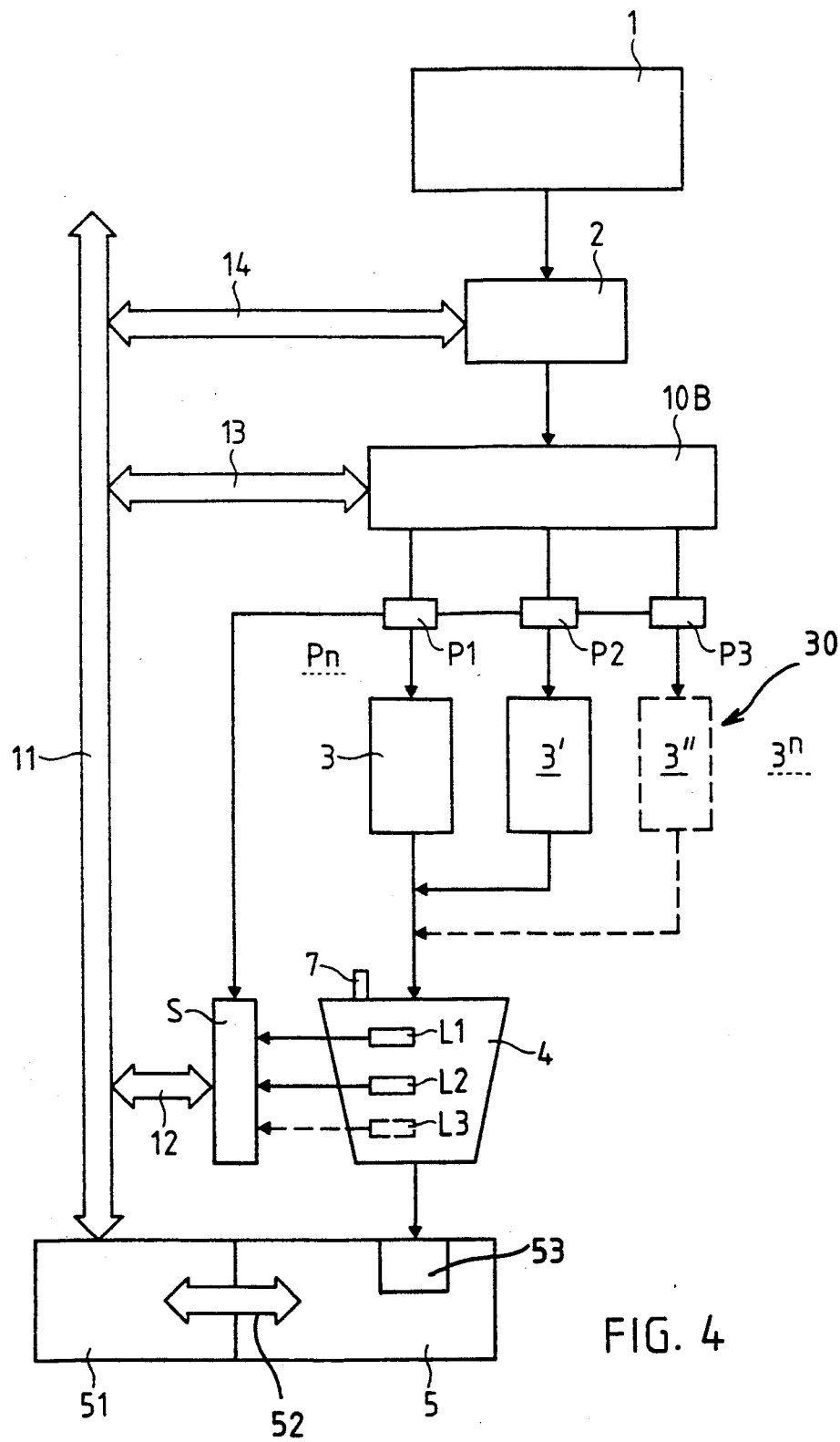
FIG. 4 is a schematic block diagram showing a fourth exemplary embodiment of the inventive filtering apparatus utilizing digital control means.

In the embodiments illustrated in FIGS. 2 through 4, of course, the by-pass filters or filter elements 3' and/or 3" will also be activated at a decrease in the filtering power or capacity which, for example, may be due to filter contamination. Progressive blocking of the filter element 3 thus not only will be detected sufficiently early but also can be optically and/or acoustically indicated. The related control signals are obtained by comparing the measured operation times of the master or main filter element 3 and the slave or secondary filter element 3' and/or 3". Whenever the slave or secondary or by-pass filter element is excessively employed, this is an indication that the master or main filter element 3 must be exchanged.

The controlled pump unit 2 continues to operate and fills the intermediate storage unit or vessel 4 after the liquid medium has been withdrawn to the receiving unit 53 of the analytical instrument such as the particle analyzer 5. This operation is continued until the liquid level in the intermediate storage unit or vessel 4 arrives from below at the level of the low level detector L2. Thereupon, the slave or secondary or by-pass filter element 3' and/or 3" is turned off or deactivated. When, as a result of the further pumping operation of the controlled pump unit 2, the level of the liquid in the intermediate storage unit or vessel 4 arrives at the level defined by the high level detector L1, the operation of the controlled pump unit 2 is interrupted until the liquid level, due to further withdrawal, again falls below the level defined by the high level detector L1. During all of the aforementioned operational steps, the intermediate storage unit or vessel 4 must be aerated and deaerated and such aeration and deaeration is effected through the deaeration filter 7.

Due to the fact that the filtering unit 30 and the aforementioned filter elements 3, 3' and 3" are operated under the action of pressure instead of the action of suction, there is prevented the formation of bubbles at the outlet of the reservoir or container 1 and the throughput through the filtering unit 30 or the filter elements 3, 3' and 3" can be controlled by correspondingly controlling the pumping pressure generated by the controlled pump unit 2. In this manner there can be adjusted a volumetric equilibrium between withdrawal and supply in terms of the volumina. The inventive filtering apparatus can also be adjusted to the frequency of the operational steps or cycles of the analytical instrument such as the particle analyzer 5 by shifting the aforementioned volumetric equilibrium with respect to the volume throughput. This is important because the inventive filtering apparatus as described hereinbefore can be used in conjunction with multiple types of apparatuses in the field of particle analysis but also is suitable for other fields of use which require on-line filtering. Such broad applicability of the inventive filtering apparatus is particularly realized by means of the just discussed exemplary embodiments of the inventive filtering apparatus.

Figure 1:
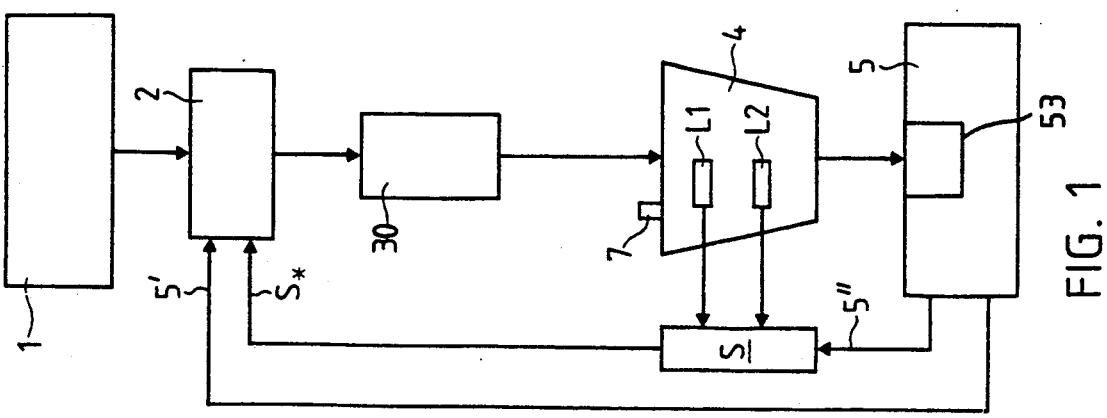
FIG. 1 is a schematic block diagram showing a first exemplary embodiment of the inventive filtering apparatus.

The first exemplary embodiment of the inventive filtering apparatus as illustrated in FIG. 1 of the drawings in the instant application, constitutes the most simple embodiment of the inventive filtering apparatus. The filtering unit 30 therein contains the aforementioned filter insert and is devoid of any by-pass filters or filter elements of the type as shown in FIGS. 2 to 4 and discussed hereinbefore. The low level detector L2 in the intermediate storage unit or vessel 4 is utilized for energizing the controlled pump unit or filtering pump 2. Thus the controlled pump unit or filtering pump 2 is inoperative or de-energized during the time the liquid level in the intermediate storage unit or vessel 4 moves in a direction from above and is located between the high level detector L1 and the low level detector L2. The controlled pump unit or filtering pump 2 is also deenergized when the liquid level within the intermediate storage unit or vessel 4 arrives at the high level detector L1 from below and the intermediate storage unit or vessel 4 is refilled. This operation of the filtering apparatus can be readily supplemented with the aforedescribed by-pass filter or filter element and the correspondingly extended control unit S and thus can be readily equipped for providing the more intelligent type of operation as described hereinbefore.

The controlled pump unit or filtering pump 2 may comprise a piston pump like the piston pump K1 or K2 illustrated in FIG. 2 for the second exemplary embodiment. Such piston pump preferably has a working or suction volume comprising a multiple of the volume of the intermediate storage unit or vessel 4. Basically, also a rotary pump, as illustrated for the third embodiment of the inventive filtering apparatus in FIG. 3, such as a centrifugal pump, wing or vane pump, gear pump or the like is suitable for this purpose. A piston pump, however, has the advantages of simple pumping pressure control and minimum inherent abrasion. The latter, of course, is essential for the intended very small or submicron particle analysis and last but not least continuous abrasion occurring in the controlled pump unit or filtering pump 2 would additionally load the filtering unit 3. Furthermore, the piston pump is better suited for intermittent operation as compared to pumps which must again build-up the appropriate flow for achieving the desired pumping action and which are more suitable for continuous operation.

Advantageously the piston pumps are made of glass, a material which generally can be considered as corrosion resistant.

The piston pump can be reversed in any conventional manner. In the event of a high frequency of the operation cycles, when the times required for returning the piston and re-filling the pump must be bridged, there is recommended the use of a second piston or piston pump which is operated in mutually opposite manner with respect to the first piston or piston pump. The two such piston pumps thus alternatingly pump the liquid medium to be filtered from the reservoir or container 1 to the filtering unit 30. If such solution of the problem is not acceptable, there will be utilized a continuously operating pump of the aforementioned types which, instead of being deenergized, is made to operate against a closed valve.

As illustrated for the embodiments shown in FIGS. 2 and 3, a controlled switching unit 10A which may constitute, for example, a multiple-way valve or selector valve can be provided. Such controlled switching unit 10A is connected downstream of the filter elements 3 and 3' when the filtering apparatus contains the piston pumps K1 and K2 as shown in FIG. 2. The controlled switching unit 10A is connected upstream of the filter elements 3 and 3' when the filtering apparatus contains a rotary pump as shown in FIG. 3. The control of the switching unit 10A is effected by means of a control signal S* which is generated by the control unit S which also controls the controlled pump unit or filtering pump 2A or 2B, as the case may be. The control signal S* may constitute a general control signal, for example, a composite control signal having a vectorial character which is indicated by the star index. This will be further discussed with reference to FIG. 4 and the inventive method.

When using the rotary pump as in the controlled pump unit or filtering pump 2B, the continuous operation can occur in two or more steps of the rotary speed of the rotary pump. For example, the rotary speed of the rotary pump for pumping the liquid medium to be filtered through either one of the filter elements 3 or 3' is only half the rotary speed which is required when the two filter elements 3 and 3' must be simultaneously supplied with the liquid medium. Such half-speed operation, for instance, may be required when one of the two filter elements 3 or 3' is blocked. Depending upon the conditions, it may then be useful to provide a further controlled switching unit 10A downstream from the filtering elements 3 and 3' and such further controlled switching unit 10A may also be controlled by means of the control unit S.

Preferably, the filtering unit 30 or the filter elements 3 and 3' have a rather small volume and the filtering surface merely is selected of such a size that the filtering unit 30 or the filter elements 3 and 3' can be utilized independently of the action of gravity. This may be important with respect to retrofitting of analytical instruments having an earlier manufacturing date where spatial constraints require flexibility of installation. Conventional filtering materials can be used for the filtering unit 30 or the filter elements 3 and 3'. Generally, commercially available filter cartridges can be used nearly unchanged and, therefore, the filtering unit 30 or the filter elements 3 and 3' will not be described herein in further detail.

It is one object of the control unit S to initiate the correct operation of the controlled pump units or filtering pumps 2, 2A and 2B in response to the signals generated by the high level detector L1 and the low level detector L2 located in the intermediate storage unit or vessel 4. In the simplest case, the operation involves energizing and deenergizing the controlled pump unit or filtering pump 2 shown in FIG. 1. In the two embodiments illustrated in FIGS. 2 and 3, the operation of the controlled pump units or filtering pumps 2A and 2B also involves the connection and disconnection of the by-pass filter or filter element 3'. Also included therein are the reversal of the piston pumps in the controlled pump unit or filtering pump 2A as well as the control of the controlled switching unit 10A which determines the flow path of the liquid medium.

The control unit S receives, in addition to the signals originating from the high level sensor L1 and the low level sensor L2 located in the intermediate storage vessel or unit 4, operation step or cycle data 5" from the analytical instrument such as the particle analyzer 5 in order to thereby control the pumping pressure and/or the frequency of the pumping operation or the throughput. A further signal path 5' leads from the analytical instrument such as the particle analyzer 5 to the controlled pump unit or filtering pump 2, 2A or 2B, as the case may be. This further signal path 5' also can be used for communicating further operating conditions in the form of parameter-related signals.

In the embodiment illustrated in FIG. 4, pressure sensors P1, P2 and P3 are provided on the input side or upstream of the respective filter elements 3, 3', 3''... 3n. The outputs of the pressure sensors P1, P2, P3... Pn are connected to the control unit S. Consequently, in addition to the signals generated by the high level detector L1 and the low level detector L2, the pressure-related signals can be utilized for controlling the amount of available filtered liquid medium.

The power or capacity of the inventive filtering apparatus can be flexibly adjusted to the absorption or take-up capacity of the receiving unit 53 in the analytical instrument such as the particle analyzer 5. However, this absorption or take-up capacity of such receiving unit 53 must be communicated to the control unit S in appropriate manner.

The control unit S further incorporates, when combined with the embodiments of the inventive filtering apparatus as illustrated in FIGS. 2 and 3, indicating means for indicating the operation of the master or main filter or filter element 3 and the by-pass or slave or secondary filter element 3' and/or 3''. Indicating means are also provided for indicating the result of the comparison of the operation times of the master or main filter 3 and the by-pass or slave or secondary filter elements 3' and/or 3''. Such indication and comparison, as already explained hereinbefore, permit a conclusion concerning the state or condition of the different filter elements.

The fourth embodiment of the inventive filtering apparatus as illustrated in FIG. 4, constitutes a filtering apparatus which is digitally operated in its entirety. From FIG. 4 of the drawings, there will also be apparent the inventive filtering method in its entirety and in an improved manner as compared with FIGS. 1 through 3. Only the essential elements of the filtering apparatus are illustrated in FIG. 4 and designated, where appropriate, with the same reference characters.

In the sequence from the top to the bottom of FIG. 4, these essential elements comprise a reservoir or container 1 containing the unfiltered or prefiltered liquid medium to be filtered, a controlled pump unit or filtering pump 2, and a controlled switching unit or distributor 10B constructed in a multiplex manner for realizing more than two filtering paths. Downstream thereof and as viewed along the flow path of the liquid medium, there are optionally provided pressure sensors P1, P2, P3... Pn for measuring the counterpressure built-up on the input side of associated filter elements 3, 3', 3''... 3n. The filter elements 3, 3', 3''... 3n are connected in mutually parallel relationship and ultimately open into a common inlet which leads to the intermediate storage unit or vessel 4 containing the high level detector L1, the low level detector L2 and optionally a further level detector L3. With regard to the flow of the liquid medium, the intermediate storage unit or vessel 4 is connected to the receiving unit 53 of the analytical instrument such as the particle analyzer 5. The analytical instrument such as the particle analyzer 5 is connected in terms of signal communication with a digital control processor 51 by means of a symbolically illustrated bus 52. Generally, the control processor 51 constitutes a computer of the PC type. However, single board or uniplate-processors which are specifically dedicated to the instant combination, are also suitable for this purpose.

A central data or system bus 11 leads from the control processor 51 to all of the controlled apparatus components which, of course, must be correspondingly addressable. The configuration illustrated in FIG. 4 is one of a number of possible configurations, however, constitutes the simplest configuration with respect to the intended method complexity. The control unit S receives all sensor- or detector-related signals, namely the output signals generated by the pressure sensors P1, P2, P3 . . . Pn and the output signals of the level detectors L1, L2 and, if present, L3. The thus received signals are communicated to the central data or system bus 11 by means of the bus 12 and thus to the control processor 51. The sensor- and detector-related signals are processed in the control processor 51 in combination with the signals communicated by the bus 52 from the analytical instrument such as the particle analyzer 5 in order to form the control parameters and the associated addresses at which a specific action is intended to be effected. The control parameter signals and the associated addresses are then conducted via the 1 central data or system bus 11 to the controlled pump unit or filtering pump 2, i.e. the associated control element via the bus 14 and the controlled switching unit or distributor 10B via the bus 13. An individual subprogram for programming the desired type of operation can be provided for the multiplex operation of the controlled switching unit or distributor 10B.

For the following consideration, it will be assumed that the controlled pump unit or filtering pump 2 comprises a rotary pump operating at controlled rotary speed. Such rotary pump also may constitute a multiple-stage rotary pump. The rotary pump substantially immediately offers the desired pumping pressure to the controlled switching unit or multiplex-operated distributor 10B for switching through to one or two or more of the filter elements 3, 3', 3''. . . 3n. Under these conditions, among others, the following operational variants are possible:

(i) All of the filter elements 3, 3', 3''. . . 3n are conjointly subjected to the output pressure of the liquid medium to be filtered; the intermediate storage unit or vessel 4, then, is rapidly filled. Depending upon the condition of the individual filter elements 3, 3', 3''. . . 3n, the pressures on the input side of such filter elements are differently rapidly built-up within this short time period and such pressure build-up is detected by the associated pressure sensors P1, P2, P3 . . . Pn. For the following operation, there is selected a filtering path exhibiting medium pressure build-up. Criteria therefore are that filter elements exhibiting rapid pressure build-up may be blocked and thus are available only for a short operation period whereas filters exhibiting slow pressure build-up are still fresh and enable long operation periods.

(ii) During the following operation, a filter element exhibiting a medium pressure build-up is connected in parallel with a filter element which exhibits the maximum pressure build-up. When the liquid medium supply exceeds the absorption or take-up capacity required for the analytical instrument such as the particle analyzer 5 beyond a predetermined limiting value, the two filter elements are operated until the liquid medium supply falls below the required absorption or take-up capacity. At this moment of time the filter element exhibiting the maximum pressure build-up is indicated by the control processor 51 as blocked and required to be exchanged. In this manner there can be obtained an optimum utilization particularly of expensive filter elements.

(iii) During the aforementioned "two-filter operation", the remaining filter elements are utilized during test runs at predetermined time intervals in order to repeatedly check their operability. From the previous pressure build-up which advantageously remains stored, it is possible to draw a conclusion concerning an eventual deterioration of the associated filter element which, then, can be utilized at an earlier time than another remaining filter elements which exhibit better pressure build-up properties. It will be self-evident that the control processor 51 is also capable of printing out the thus detected pressure build-up properties of the filter elements in individual filter element records. In this connection reference is made to the fact that the inventive filtering apparatus can be utilized for centrally supplying filtered liquid medium to a multitude of analytical instruments which possibly have different absorption or take-up capacities and operate during operation periods at randomly selected times.

(iv) The exchange of one or more of the filter elements 3, 3', 3''. . . 3n is communicated to the control processor 51 in order that the control processor 51 may interrupt the supply of liquid medium via the controlled switching unit or multiplex-operated distributor 10B to those flow paths in which the individual filter elements are being exchanged. During such exchange periods, the other filter elements are operated in the same optimum manner as described hereinbefore and thus maintain in operation the analytical instrument such as the particle analyzer 5.

The recognition parameters for identifying individual ones of the filter elements 3, 3', 3''. . . 3n are related to, among others, the pressure build-up properties. The data sets associated with each one of such filter elements 3, 3', 3''. . . 3n can be stored in a "library" of the analytical instrument such as the particle analyzer 5 and can be selected from the library by means of a menu which is presented on a display screen. The association of the data with the utilized one of the filter elements 3, 3', 3''. . . 3n simplifies monitoring the filtering apparatus with respect to whether or not the correct filter element has been incorporated therein.

It will be immediately seen that the operative reliability thus is increased in a more than proportional manner. The methods and filtering apparatuses discussed hereinbefore permit recognizing exhausted or blocked filter elements, fresh filter elements, little used and nearly exhausted filter elements; also, the service life of the filter elements can be detected. Furthermore, the parallelity which results from the information and reliability and the thus produced redundancy, can be relied upon at any time in order to immediately serve or be adapted to the given absorption or take-up capacities of one or more analytical instruments such as particle analyzers 5. The data can be used for operating the entire filtering apparatus by indicating which filter elements must be exchanged, which filter elements should be put into operation earlier than others and not in the last place, and which filter element has become prematurely inoperable within its service life and must be exchanged although it has been little used. Clearly, there is thus also facilitated the management of a plurality of analytical instruments. Furthermore, there can be detected the incorporation of a wrongly selected type of filter element whereby the reliability of operation is further increased.

Using the inventive filtering apparatus as described hereinbefore, there is enabled reliable operation under high load. Operational reliability is also ensured in the event of deviations from the required medium operational condition. In an extreme case, such deviations may imply the use of an extra volume of filtered liquid medium, i.e. an additional withdrawal in the order of magnitude of a full supply volume outside the usual withdrawal times. The filtering apparatus is quite capable of processing this additional amount of liquid medium during the automatic operation. Even if the probability of such extreme occurrence can be assumed to be relatively small, an automatic operation at high processing rates otherwise could be significantly disturbed at the occurrence of such event and eventually may even be interrupted or set onto a false course.

The method as described herein is suitable for supplying one or a number of analytical instruments with filtered liquid medium. Essentially, when carrying out the inventive method, there is detected the filtering state or condition of the filter elements and such filter elements are used in accordance with their operability by controlling a supply pump such as the controlled pump unit or filtering pump 2 in response to the detected liquid level variation in the pressure variation at the filter elements 3, 3', 3"... 3n which are arranged intermediate the supply pump or controlled pump unit or filtering pump 2 and the intermediate storage or unit or supply vessel 4.

Thus, there are used, for instance, two filter elements during operation of the filtering apparatus whereas the remaining filter elements are in a standby condition. During such standby condition, the remaining filters are included in the main operation for control purposes at predetermined time intervals for brief periods of time. Furthermore, there can be selected for the operation from the plurality or set of filter elements, a filter element exhibiting a medium pressure build-up against the pumping pressure and a filter element exhibiting the maximum pressure build-up against the pumping pressure. The filter element exhibiting the maximum pressure build-up rate constitutes the most exhausted or most blocked filter element of the entire battery or set of filtering elements and thus can be used in an optimum or even maximum manner.

A filter element exhibiting a pressure build-up which exceeds a predetermined threshold value, can be excluded from the main operation and a different filter element having a smaller pressure build-up can be put into operation. Filter elements having unspecific properties in comparison to the specific pressure build-up properties of the incorporated type of filter elements, can be either excluded from the operation and/or indicated and/or recorded. With respect to the inventive method there is thus provided an extremely wide latitude which can be utilized by employing the respectively required measures.

While there are shown and described present preferred embodiments of the invention, it is to be distinctly . understood that the invention is not limited thereto, but may be otherwise variously embodied and practiced within the scope of the following claims. Accordingly,

What we claim is:

1. A filtering apparatus adaptable for use with at least one analytical instrument, comprising:
    a controlled pump unit having an inlet side and an outlet side;
    a reservoir for storing a liquid medium to be filtered and connected to said inlet side of said controlled pump unit;
    a filtering unit connected to said outlet side of said controlled pump unit;
    an intermediate storage unit connected to said filtering unit, wherein the at least one analytical instrument is adaptable to said intermediate storage unit;
    said intermediate storage unit receiving filtered liquid medium from said filtering unit for feeding said filtered liquid medium to said at least one analytical instrument;
    a control unit for controlling the operation of said controlled pump unit;
    liquid level detection means located in said intermediate storage unit and responding to the liquid level of said filtered liquid medium present in said intermediate storage unit;
    said liquid level detection means being connected to said control unit; and
    said control unit comprising means responsive to the liquid level detected in said intermediate storage unit by said liquid level detection means for controlling the operation of the controlled pump unit.

2. The filtering apparatus as defined in claim 1, further including:
    a receiving unit adaptable to said at least one analytical instrument;
    said receiving unit possessing a predetermined take-up capacity for receiving filtered liquid medium from said intermediate storage unit;
    said liquid level detection means located in said intermediate storage means, containing a high level detector and a low level detector; and
    said high level detector and said low level detector defining in said intermediate storage unit a volume capacity of filtered liquid medium greater than said predetermined take-up capacity of said receiving unit.

3. The filtering apparatus as defined in claim 2, wherein:
    said volume capacity defined by said high level detector and said low level detector in said intermediate storage unit being greater than said take-up capacity of said receiving unit adaptable to said at least one analytical instrument by a factor greater than 1 and smaller than 2.

4. The filtering apparatus as defined in claim 1, wherein:
    said filtering unit contains two filter elements connected for parallel operation;
    a first one of said two filter elements being operated under the control of said control unit; and
    a second one of said two filter elements being placed into operation additionally to said first filter element under the control of said control unit.

5. The filtering apparatus as defined in claim 4, wherein:
    said liquid level detection means comprise a high level detector and a low level detector; and
    the response of said low level detector defining a predetermined operating condition under which said second filter element is additionally placed into operation.

6. The filtering apparatus as defined in claim 4, wherein:
    said controlled pump unit contains at least one piston pump which is controlled with respect to pumping speed and pump pressure by means of said control unit;
    said control unit being adaptable to said at least one analytical instrument;
    said control unit receiving from said at least one analytical instrument a signal sequence indicative of the operating sequence of the at least one analytical instrument; and
    said control unit controlling an operating sequence of said controlled pump unit in response to said signal sequence received from said at least one analytical instrument.

7. The filtering apparatus as defined in claim 1, wherein:
said controlled pump unit contains at least one piston pump which is controlled with respect to pumping rate and pump pressure by means of said control unit;
said control unit being adaptable to said at least one analytical instrument;
said control unit receiving from said at least one analytical instrument a signal sequence indicative of the operating sequence of the at least one analytical instrument; and
said control unit controlling an operating sequence of said controlled pump unit in response to said signal sequence received from said at least one analytical instrument.

8. The filtering apparatus as defined in claim 7, wherein:
said controlled pump unit contains two piston pumps;
said two piston pumps being connected such as to operate in mutually opposite manner and to alternatingly supply the liquid medium to be filtered to said filtering unit;
a controlled switching unit interconnecting said controlled pump unit and said filtering unit;
said controlled switching unit being connected to said control unit; and
said controlled switching unit being switched under the action of said control unit such as to direct the liquid medium alternatingly issuing from said two piston pumps to said filtering unit.

9. The filtering apparatus as defined in claim 1, wherein:
said controlled pump unit contains a predetermined number of pumps for pumping said liquid medium to be filtered from said reservoir to said filtering unit;
said filtering unit containing at least two filter elements;
a controlled switching unit connected to said control unit; and
said controlled switching unit being connected to said filtering unit and being switched under the action of said control unit such as to selectively connect a preselected number of said at least two filter elements to said intermediate storage unit.

10. The filtering apparatus as defined in claim 9, wherein:
said predetermined number of pumps of said controlled pump unit constitutes at least two piston pumps;
said one of said at least two piston pumps being contiguous to one of said at least two filter elements in said filtering unit;
said control unit energizing a preselected number of said at least two piston pumps;
said controlled switching unit interconnecting said filtering unit and said intermediate storage unit; and
said controlled switching unit being switched under the control of said control unit such as to selectively connect said filter elements associated with said preselected number of piston pumps to said intermediate storage unit.

11. The filtering apparatus as defined in claim 9, wherein:
said predetermined number of pumps of said controlled pump unit constitutes a rotary pump;
said control unit controlling the rotary speed of said rotary pump;
said controlled switching unit interconnecting said controlled rotary pump and said filtering unit; and
said controlled switching unit being switched under the control of said control unit such as to selectively connect a predetermined number of said at least two filter elements to said intermediate storage unit as a function of said rotary speed of said controlled rotary pump.

12. The apparatus as defined in claim 11, further including:
a further controlled switching unit interconnecting said filtering unit and said intermediate storage unit;
said further controlled switching unit being controlled by said control unit; and
said further controlled switching unit being switched under the control of said control unit such as to selectively connect said predetermined number of said at least two filter elements to said intermediate storage unit as a function of said rotary speed of said controlled rotary pump.

13. The filtering apparatus as defined in claim 1, wherein:
said controlled pump unit contains at least one piston pump;
said at least one piston pump possessing a predetermined suction volume;
said intermediate storage unit possessing a predetermined volume capacity; and
said predetermined suction volume of said at least one piston pump constituting a multiple of said predetermined volume capacity of said intermediate storage unit.

14. The apparatus as defined in claim 1, further including:
a control processor adaptable to said analytical instrument;
a system bus connecting said control processor with said controlled pump unit and said control unit;
a controlled switching unit interconnecting said controlled pump unit and said filtering unit;
said controlled switching unit being constructed as a multiplexer unit connected to said system bus;
said filtering unit containing a plurality of filter elements;
said controlled switching unit distributing the liquid medium issuing from said controlled pump unit over preselected ones of said plurality of filter elements in a programmable manner; and
said control unit constituting a digitally operated control unit.

15. The filtering apparatus as defined in claim 14, further including:
a plurality of pressure sensors provided between said controlled switching unit and an input side of associated ones of said plurality of filter elements; and
said plurality of pressure sensors being connected to said control unit.

16. The filtering apparatus as defined in claim 14, wherein:
said liquid level detection means comprise a high level detector, a low level detector and at least one further level detector.

17. The filtering apparatus as defined in claim 1, wherein:
said liquid level detection means comprise a high level detector, a low level detector and at least one further level detector.

18. The filtering apparatus as defined in claim 1, in combination with at least one analytical instrument.

19. The filtering apparatus in combination with said at least one analytical instrument as defined in claim 18, wherein:
said at least one analytical instrument constitutes at least one particle analyzer.

20. A method of feeding a filtered liquid medium to at least one receiving unit, comprising the steps of:
pumping under pressure a liquid medium to be filtered through a filtering unit to an intermediate storage unit for discharge to at least one receiving unit;
detecting level variations of said filtered liquid medium in said intermediate storage unit;
measuring pressure variations appearing on the input side of said filtering unit; and
controlling the pumping operation as a function of the level variation of said filtered liquid medium in said intermediate storage unit and the pressure variations appearing on the input side of said filtering unit.

21. The method as defined in claim 20, further including the steps of:
connecting a plurality of filter elements in parallel to each other in said filtering unit;
during said step of pumping said liquid medium to be filtered through said filtering unit, pumping said liquid medium to be filtered through a maximum of two of said plurality of filter elements;
placing remaining filter elements of said plurality of filter elements into a standby condition during said pumping operation; and
transiently and at predetermined time intervals, incorporating said remaining filter elements in said pumping operation for control purposes during the time the remaining filter elements are in said standby condition.

22. The method as defined in claim 21, further including the steps of:
detecting pressure build-up at said plurality of filter elements of said filtering unit during said pumping operation; and
selecting for said pumping operation and as said maximum of two filter elements, a filter element exhibiting a medium rate of said pressure build-up and a filter element exhibiting a maximum rate of said pressure build-up.

23. The method as defined in claim 22, further including the steps of:
defining a threshold value for the rate of said pressure build-up; and
during said pumping operation, placing a filter element exhibiting a pressure build-up rate exceeding said threshold value out of operation and placing into operation a filter element exhibiting a pressure build-up rate lower than said threshold value.

24. The method as defined in claim 21, further including the steps of:
selecting as said plurality of filter elements, a predetermined number of filter elements exhibiting a predetermined pressure build-up during said pumping operation;
detecting pressure build-up at individual ones of said plurality of filter elements during said pumping operation; and
during said pumping operation, indicating for said plurality of filter elements, individual filter elements exhibiting a pressure build-up different from said predetermined pressure build-up.

25. The method as defined in claim 24, further including the step of:
recording said individual filter elements which exhibit said pressure build-up different from said predetermined pressure build-up.

26. The method as defined in claim 24, further including the step of:
excluding from said pumping operation, said individual filter elements which exhibit said pressure build-up different from said predetermined pressure build-up.

27. The method as defined in claim 20, further including the steps of:
connecting a plurality of filter elements in parallel to each other in said filtering unit; and
during said step of pumping said liquid medium to be filtered through said filtering unit, distributing said liquid medium over said plurality of filter elements in a multiplex operation.

28. A filtering method for supplying a filtered liquid medium to at least one analytical instrument, comprising the steps of:
storing at least a predetermined volume of filtered liquid medium in an intermediate storage unit;
discharging said predetermined volume of said stored filtered liquid medium into a receiving unit associated with the at least one analytical instrument in accordance with a sequence of operational steps of said at least one analytical instrument;
during said step of discharging said predetermined volume of said stored filtered liquid medium from said intermediate storage unit, withdrawing said liquid medium in an unfiltered condition from a reservoir and pumping said unfiltered liquid medium under pressure through a filtering unit into said intermediate storage unit;
said pumping operation entailing the step of refilling said intermediate storage unit with said predetermined volume of filtered liquid medium at a predetermined pumping rate;
detecting in said intermediate storage unit, at least one predeterminate liquid level indicative of the presence of said predetermined volume of filtered liquid medium in said intermediate storage unit; and
controlling said pumping operation in response to said sequence of operational steps of said at least one analytical instrument and as a function of the level of filtered liquid medium present in said intermediate storage unit.

29. The filtering method as defined in claim 28, wherein:
said step of detecting said at least one predeterminate liquid level in said intermediate storage unit entails detecting a high liquid level and a low liquid level;
starting said pumping operation once said liquid level in said intermediate storage unit falls below said high liquid level;
increasing said predetermined pumping rate whenever the liquid level of said filtered liquid medium in said intermediate storage unit is below said low liquid level; and interrupting said pumping operation once said liquid level in said intermediate storage unit rises to said high liquid level.

30. The filtering method as defined in claim 29, further including the steps of:

defining as said predetermined volume, a predetermined take-up capacity of said receiving unit associated with said at least one analytical instrument;

storing in said intermediate storage unit a preselected volume of filtered liquid medium greater than said predetermined take-up capacity of said receiving unit associated with said at least one analytical instrument; and defining in said intermediate storage unit between said high liquid level and said low liquid level, a liquid volume greater than said predetermined volume of filtered liquid medium by a factor greater than 1 and smaller than 2.

31. The filtering method as defined in claim 29, further including the steps of:

connecting at least two filter elements parallel to each other in said filtering unit;

connecting at least two piston pumps to respective ones of said at least two filter elements;

using one of said at least two piston pumps and the respective one of said at least two filter elements during said pumping operation;

additionally energizing at least one further pump of said at least two piston pumps and operating at least one further respective filter element of said at least two filter elements as long as the liquid level of said filtered liquid medium in said intermediate storage unit is below said low liquid level;

selectively connecting the operative ones of said at least two filter elements to said intermediate storage unit by means of a controlled switching unit; and controlling the adjustment of said controlled switching unit as a function of the level of filtered liquid medium in said intermediate storage unit.

32. The filtering method as defined in claim 29, further including the steps of:

connecting at least two filter elements parallel to each other in said filtering unit;

using a variable-speed rotary pump operating at least at two different rotary speeds for said pumping operation;

using one of said at least two different rotary speeds and a respective one of said at least two filter elements during said pumping operation;

switching to at least one further rotary speed of said at least two different rotary speeds of said variable-speed rotary pump and additionally operating at least one further respective filter element of said at least two filter elements as long as the level of said filtered liquid medium in said intermediate storage unit is below said low liquid level;

selectively connecting said rotary pump to the operative ones of said at least two filter elements by means of a controlled switching unit; and controlling the adjustment of said controlled switching unit as a function of the level of filtered liquid medium in said intermediate storage unit.

33. The filtering method as defined in claim 28, further including the steps of:

selecting at least one piston pump for carrying out said pumping operation; and controlling said at least one piston pump with respect to pumping rate and pump pressure.

34. The filtering method as defined in claim 33, wherein:

said step of selecting said at least one piston pump entails selecting a piston pump having a suction volume constituting a multiple of said predetermined volume of filtered liquid medium stored in said intermediate storage unit.

35. The filtering method as defined in claim 33, further including the steps of:

connecting, as said at least one piston pump, two piston pumps in parallel to each other to said filtering unit; and operating said two piston pumps in mutually opposite manner in an immediately successive, alternating fashion and thereby continuously pumping said unfiltered liquid medium through said filtering unit.

36. The filtering method as defined in claim 28, further including the step of:

selecting as said filtering unit, a filtering unit containing a filter insert for separating a liquid medium from submicron size particles suspended in said liquid medium.

37. The filtering method as defined in claim 28, further including the step of:

selecting at least one particle analyzer as said at least one analytical instrument.

* * * * *